United States Patent [19]

Sprecker et al.

[11] 4,242,281
[45] Dec. 30, 1980

[54] PROCESS FOR PREPARING 6-HYDROXY-2,6-DIMETHYLHEPTANAL AND INTERMEDIATES THEREOF

[75] Inventors: Mark A. Sprecker, Sea Bright; Robert W. Trenkle, Bricktown; Braja D. Mookherjee, Holmdel; Manfred H. Vock, Locust; Joaquin F. Vinals, Red Bank, all of N.J.; Jacob Kiwala, Brooklyn, N.Y.; Frederick L. Schmitt, Holmdel, N.J.

[73] Assignee: International Flavors & Fragrances Inc., New York, N.Y.

[21] Appl. No.: 88,519

[22] Filed: Oct. 26, 1979

Related U.S. Application Data

[62] Division of Ser. No. 52,355, Jun. 27, 1979, abandoned, which is a division of Ser. No. 961,685, Nov. 17, 1978, abandoned.

[51] Int. Cl.³ .............................................. C07C 47/19
[52] U.S. Cl. ..................................... 568/458; 568/496
[58] Field of Search .......................................... 260/602

[56] References Cited

U.S. PATENT DOCUMENTS

| | | | |
|---|---|---|---|
| 3,869,517 | 4/1975 | Gradeffi et al. | 260/602 |
| 3,917,713 | 11/1975 | Gradeffie et al. | 260/602 |
| 3,919,324 | 11/1975 | Himmele et al. | 260/602 |
| 3,935,205 | 1/1976 | Ochsner | 260/246 B |

FOREIGN PATENT DOCUMENTS

| | | | |
|---|---|---|---|
| 2045888 | 4/1971 | Fed. Rep. of Germany | 260/602 |
| 2441030 | 4/1975 | Fed. Rep. of Germany | 260/602 |
| 7605749 | 5/1976 | Netherlands | 260/602 |
| 1301597 | 12/1972 | United Kingdom | 260/602 |
| 1330848 | 9/1973 | United Kingdom | 260/602 |

OTHER PUBLICATIONS

Kogami et al., "Canadian J. of Chemistry", vol. 52, p. 125 (1974).

Primary Examiner—Werren B. Lone
Attorney, Agent, or Firm—Arthur L. Liberman

[57] ABSTRACT

Described is the compound 6-hydroxy-2,6-dimethylheptanal useful in augmenting or enhancing the aroma or taste of foodstuffs, flavoring compositions for foodstuffs, tobacco compositions, flavoring compositions for tobacco, perfume compositions, ingredients for perfume compositions, perfumed articles and ingredients for perfumed articles as well as a process for preparing 6-hydroxy-2,6-dimethylheptanal comprising the steps of:

(i) forming a sulfite addition salt of 2,6-dimethyl-5-heptenal by mixing an alkali metal sulfite in boric acid with 2,6-dimethyl-5-heptenal and (ii) hydrating the thus formed 2,6-dimethyl-5-heptenal sulfite addition salt with a hydrating reagent as well as the intermediate which is the sulfite addition salt of 2,6-dimethyl-5-heptenal.

1 Claim, 9 Drawing Figures

GC PROFILE, EXAMPLE I.

G C PROFILE, EXAMPLE I.

GC PROFILE, EXAMPLE I

GC PROFILE, EXAMPLE II.

NMR SPECTRUM, EXAMPLE II.

FIG.5 IR SPECTRUM, EXAMPLE II.

FIG. 6 GLC PROFILE, EXAMPLE IV.

FIG. 7 NMR SPECTRUM, EXAMPLE IV.

I R SPECTRUM, EXAMPLE V.

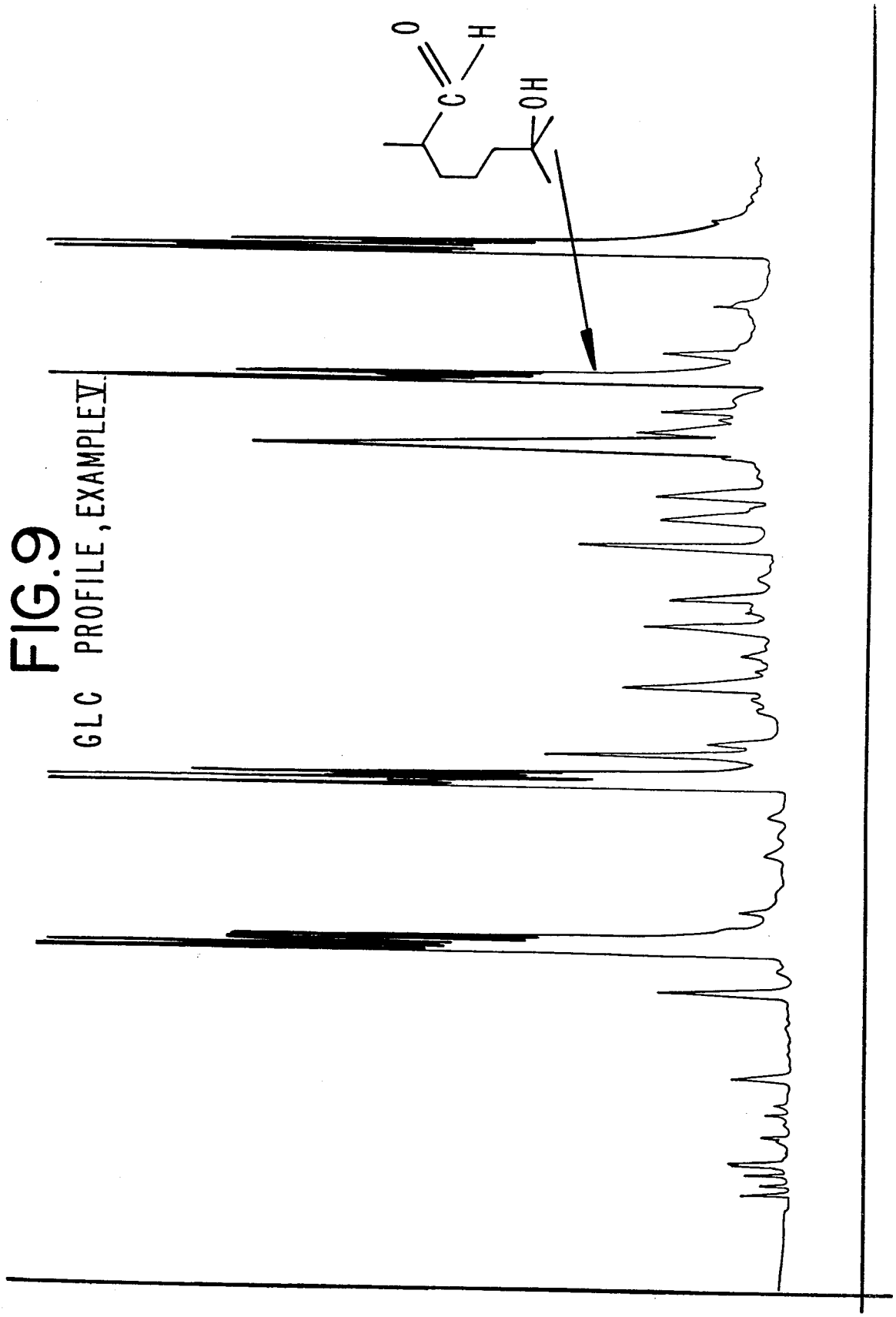
FIG. 9 GLC PROFILE, EXAMPLE V.

PROCESS FOR PREPARING 6-HYDROXY-2,6-DIMETHYLHEPTANAL AND INTERMEDIATES THEREOF

This Application is a divisional of application for U.S. Pat. Ser. No. 052,355 filed on June 27, 1979, now abandoned, which in turn is a divisional of application for U.S. Pat. Ser. No. 961,685, filed on Nov. 17, 1978, now abandoned.

BACKGROUND OF THE INVENTION

The present invention relates to the compound 6-hydroxy-2,6-dimethylheptanal to augment or enhance the flavor and/or aroma of consumable materials, e.g., tobacco, foodstuffs, perfume compositions and perfumed articles.

There has been considerable work performed relating to substances which can be used to impart (or enhance) flavors to (or in) various consumable materials. These substances are used to diminish the use of natural materials, some of which may be in short supply and to provide more uniform properties in the finished product.

Sweet, green, melony, tropical fruit-like, seedy and raspberry-like aromas and tastes are particularly desirable for many uses in foodstuff flavors, particularly natural raspberry flavors. Sweet, green, melony, floral, muguet-like aromas are particularly desirable for use in perfume compositions and perfumed articles such as soaps, detergents, fabric softener compositions, and clothes dryer aroma imparting compositions. Sweet, fruity-melon-like, peack-like, floral and aromatic sweet tabacco-like notes are particularly desirable for smoking tobacco flavoring compositions, particularly where no offnotes are imparted thereto.

Arctander, "Perfume and Flavor Chemicals" 1969, Volume 1 at monograph 1728 discloses the use in perfume compositions, perfumed articles and foodstuff flavors of "Hydroxycitronellal" as follows:

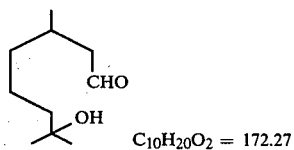

$C_{10}H_{20}O_2 = 172.27$

Colorless oily or viscous liquid. Sp.Gr.0.93.B.P.241° C.

Very slightly soluble in water, soluble in alcohol and oils. Poorly soluble in mineral oil and Glycerin or Propylene glycol.

Very slightly soluble in water, soluble in alcohol and oils. Poorly soluble in mineral oil and Glycerin or Propylene glycol.

Sweet-floral, at first delicate and refreshingly mild, but often increasing in odor strength after short olfactory study. The floral notes are mild, light and resemble Lily of the Valley. The tenacity is good, and the odor diffusion increases significantly when the material is properly blended with lower boiling odorants or modifiers.

There is a marked difference in the topnote of this material from different suppliers. Only few manufacturers make a material with a truly uniform, delicately floral odor performance from the very first (initial) note to the terminal notes (dryout, dry-down-notes).

The odor will remain for days, weeks or even longer, but the material on a testing blotter is obviously exposed to air attack and polymerization. A good way-but a very strict one-to evaluate this aldehyde is in lukewarm water. It is sufficiently soluble that it will show water-insoluble impurities stronly enhanced on this test. A very fine grade of Hydroxycitronellal will have almost the same odor on this test as it has on a perfume blotter.

Hydroxycitronellal has a sweet-floral taste, but shows a bitter aftertaste at concentrations higher than 20 ppm, sometimes even much lower than that.

This aldehyde is one of the most frequently used floralizing perfume materials. Originally introduced as a "Muguet" material, it finds its way into almost every type of floral fragrance, and a great many nonfloral ones. Its concentration in perfumes may vary from about 1% (which rarely gives effect unless supported by parallel materials) up to 30 or 40% in straight floral types.

It is almost a "must" in Muguet (at certain price levels) and Peony, Lily, Sweet Pea, Narcisse, Lindenblossom, etc. and it had a monopoly on these types for more than 40 years during which period not one material appeared that could truly replace Hydroxycitronellal. And even after the appearance of one of several very good, perhaps superior materials, the demand for Hydroxycitronellal kept increasing. Endless discussions about its possibly irritating effect on the human skin have hardly died out yet but Hydroxycitronellal has now reached and by-passed the one-million-pounds per year mark in a volume class reserved for comparatively few perfume materials.

For soap perfumes it is customary to use a slightly more "rough" grade of this material. Power is often of paramount interest to the soap manufacturer when it comes to perfuming, and the very pure grade materials with delicate odors often fail to yield the desirable power in a soap.

High-grade Hydroxycitronellal is used sparingly in flavor compositions as a floralizer in many types of flavors: Berry complexes, Citrus, Violet, Cherry, etc. and in general, a discrete touch of floral note in a flavor tend to give impression of "richness" or "body" which are highly desirable virtues. In some cases, a complete Muguet base is added to a flavor—fruit, Mint, etc.—to lend this "rounding-off" effect. The amounts needed are mere traces.

Hydroxycitronellal enters these flavor types at the concentration equal to 0.3 to 15 ppm in the finished product.

Prod.: (many methods) e.g. from Myrcene, via Myrcene dihydrochloride to Dichloro di-methyloctene. This is converted to Chloro di-hydrogeranyl acetate (and-neryl acetate) with Sodium Acetate in Benzene in presence of Triethylamine. The acetates are saponified with Calcium hydroxide to yield Hydroxycitronellol, from which the aldehyde is prepared by oxidation.

Older methods start from Citronellal via the Bisulfite which is hydrated to yield Hydroxycitronellal.

"G.R.A.S. F.E.M.A. No. 2583."

Hydroxycitronellal differs from 6-hydroxy-2,6-dimethylheptanal not only in structure but in the unexpected differences in organoleptic properties insofar as perfumery, foodstuff flavoring and smoking tobacco flavoring is concerned.

Thus, the 6-hydroxy-2,6-dimethylheptanal of our invention has unexpected, unobvious, advantageous organoleptic properties insofar as quality and substantivity of aroma and flavor with respect to hydroxycitronellal which is disclosed by Arctander.

United Kingdom Pat. No. 1,330,848 discloses the preparation of hydroxycitronellal (called "7-hydroxy-dihydrocitronellal") from citronellal itself by means of the reaction of citronellal with a secondary amine at a temperature below ambient temperature; and then transforming the thus-obtained derivative by treatment in aqueous acid medium at a temperature in the range of from −30° C. to 0° C. into a citronellal-immonium ion; and then hydrating the citronellal-immonium ion at ambient temperature; and then hydrolyzing the thus formed 7-hydroxy-dihydrocitronellal immonium ion by strong base into 7-hydroxy-dihydrocitronellal keeping the temperature within limits such that the salt which is formed during the hydrolysis reaction remains in solution all operations taking place in the liquid phase.

German Offenlengungsschrift No. 2,441,030 assigned to the Gividuan Corporation discloses a process for preparing Lyral having the structure:

[structure: OH ... CHO with cyclohexene ring labeled 4, 5]

reacting a compound having the structure:

[structure: ... CHO with cyclohexene ring labeled 4, 5]

with morpholine to form an aminal having the formula:

[structure showing cyclohexene with CH attached to two morpholine (N–O) rings, labeled 4, 4', 5]

and then hydrating the double bond of the aminal to form the hydroxy aminal and finally decomposing the hydroxy aminal to form the compound having the structure:

[structure: OH ... CHO with cyclohexene ring labeled 4, 5]

The compounds produced according to the prior art references are different in kind from the compound 6-hydroxy-2,6-dimethylheptanal produced in the instant case, 6-hydroxy-2,6-dimethylheptanal being different in chemical structure and in organoleptic properties from any of the relevant compounds of the prior art or any of the compounds formed by the processes which are relevant in the prior art.

BRIEF DESCRIPTION OF THE DRAWINGS

FIG. 9 is the GC profile for 6-hydroxy-2,6-dimethyl-heptanal produced from 2,6-dimethyl-5-heptenal according to Example V.

THE INVENTION

Figure 1:
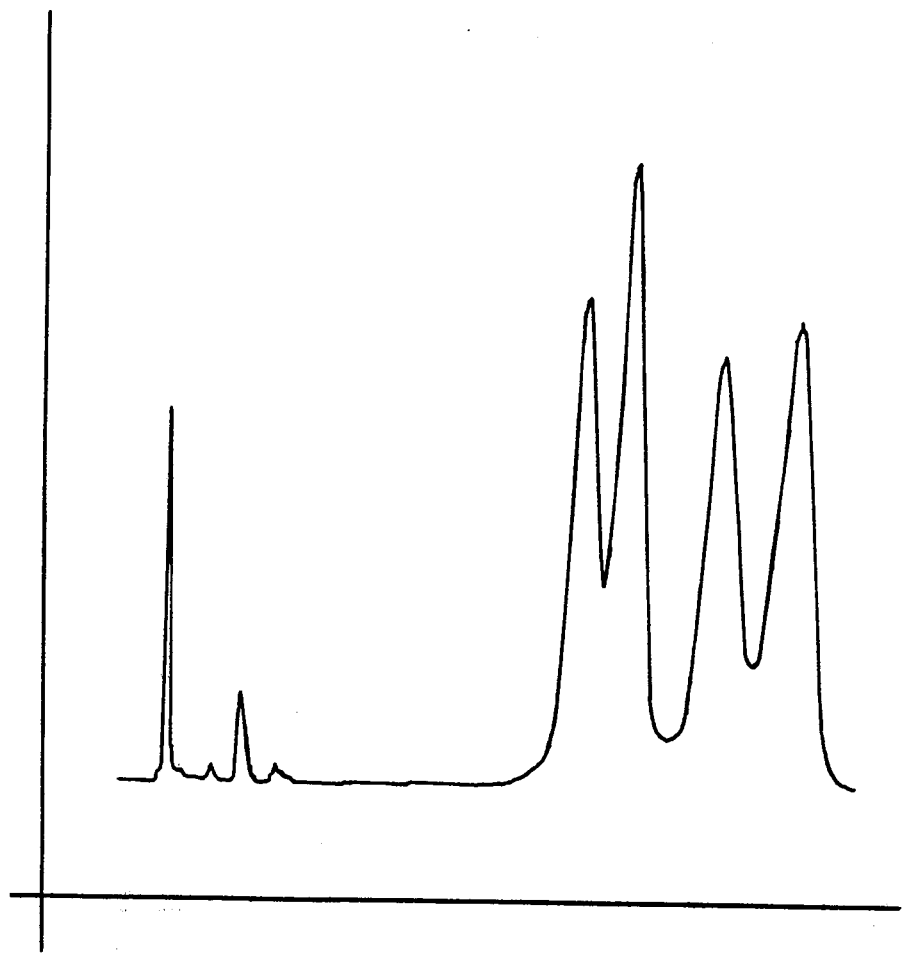
FIG. 1 is the GC profile of the reaction product of Example I after addition of sodium methoxide to the mixture of 6-methyl-5-hepten-2-one and ethyl chloroacetate.

It has now been discovered that solid and liquid foodstuff and flavoring compositions having sweet, green, melon-like, tropical fruit-like, seedy and raspberry aromas and/or flavors; and novel perfume compositions and perfumed articles and colognes having sweet, green, melony, floral and muguet-like aromas; and smoking tobacco flavoring compositions capable of imparting, augmenting or enhancing sweet, fruity-melon-like, peach-like and floral characteristics to smoking tobacco and smoking tobacco articles, e.g. cigarettes may be provided by the utilization of 6-hydroxy-2,6-dimethyl-heptanal or stereoisomers thereof.

The 6-hydroxy-2,6-dimethylheptanal useful in our invention has the structure:

[structure: OH ... C(=O)H]

and includes the dextro and laevo stereo isomers having the structures:

[structure: OH ... CH$_3$ ... C(=O)H]

and

-continued

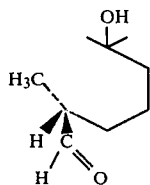

The 6-hydroxy-2,6-dimethylheptanal of our invention may be produced by hydration of 2,6-dimethyl-5-heptenal having the structure:

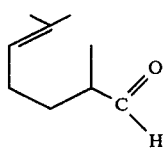

or the dextro or laevo stereo isomer thereof having one of the structures:

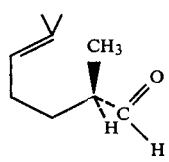

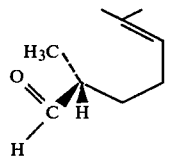

by first protecting the aldehyde moiety by means of bisulfite salt addition or by means of formation of an immonium salt or an enamine salt (e.g., using morpholine as taught by Kogami et al at Vol. 52, *Canadian Journal of Chemistry*, page 125, 1974); then hydrating the double bond using for example 60% sulfuric acid in aqueous solution; or the hydration may be by means of first forming the sulfite salt of the aldehyde using a sodium sulfite-boric acid reagent (thereby protecting the "aldehyde" moiety); followed by hydrochloric acid hydration of the sulfite salt to form 6-hydroxy-2,6-dimethylheptanal. These reaction sequences are illustrated as follows:

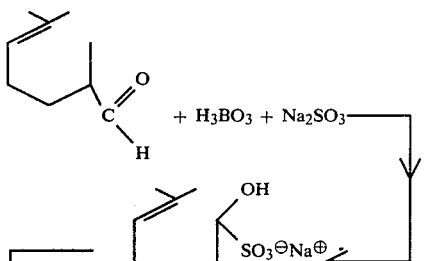

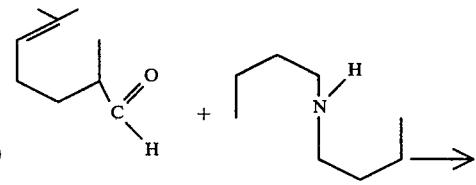

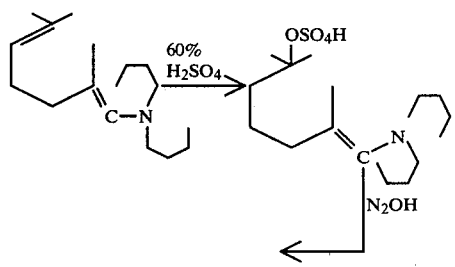

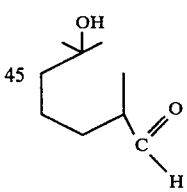

The 2,6-dimethyl-5-heptenal may be isolated from Java Citronella Oil by standard isolation means, e.g., column chromatography on an industrial scale; or it may be synthesized by reaction of 6-methyl-5-hepten-2-one and ethyl chloroacetate in the presence of an alkali metal alkoxide such as sodium methoxide according to the following reaction scheme:

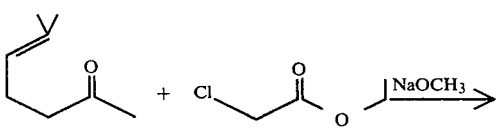

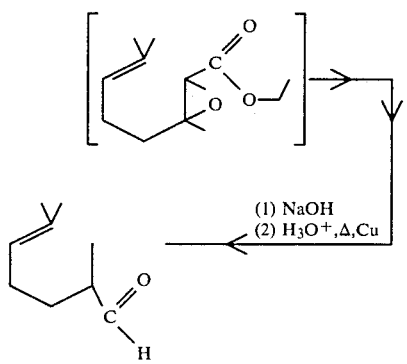

In hydrating the 2,6-dimethyl-5-heptenal using the sodium sulfite/hydrochloric acid system, the hydration reaction is to take place in an emulsion of 2,6-dimethyl-5-heptenal with water using an emulsifying agent such as sodium oleate or potassium oleate or any other alkali metal salt of a long chain fatty acid. Sodium sulfite is reacted with the 2,6-dimethyl-5-heptenal in the presence of boric acid while it is in this emulsion whereby the sulfite-aldehyde addition salt of 2,6-dimethyl-5-heptenal is formed. The reaction preferably takes place at a temperature of between 10° C. and 50° C. with a temperature of 25°–30° C. preferred. The mole ratio of sodium sulfite: 2,6-dimethyl-5-heptenal may vary between 1:1 up to 10:1 with a preferred mole ratio of approximately 4:1. The concentration of sodium sulfite in the reaction mass is preferably from 0.1 molar up to 3.0 molar and the concentration of 2,6-dimethyl-5-heptenal is from 0.5 molar up to 2.0 molar. The hydrolysis reaction with hydrochloric acid preferably takes place using from 10% up to 50% hydrochloric acid with a preferred concentration of hydrochloric acid used being 30%. The mole ratio of HCl: sulfite addition of salt of 2,6-dimethyl-6-hydroxy-heptanal is preferably 1:1 but mole ratios from 0.5:1 up to 1.5:1 may be used. The reaction temperature for the hydrolysis reaction may vary from 0° C. up to 50° C. with a preferred reaction temperature of from between 25°–35° C.

When the 6-hydroxy-2,6-dimethylheptanal or stereoisomer thereof of our invention are used as food flavor adjuvants, the nature of the co-ingredients included with the said 6-hydroxy-2,6-dimethylheptanal in formulating the product composition will also serve to alter, modify, aument or enhance the organoleptic characteristics of the ultimate foodstuff treated therewith.

As used here in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor notes.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay rubber, or certain comestible natural or synthetic resins or waxes. Incorporated with the gum base in admixture therewith may be plasticizers or softening agents, e.g., glycerine; and a flavoring composition which incorporates the 6-hydroxy-2,6-dimethylheptanal (or stereoisomer thereof) of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g, sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include aldehydes, esters, natural oils, alcohols, sulfides, ketones, lactones, carboxylic acids and hydrocarbons such as heliotropin, terpinenol-4, benzaldehyde, anisaldehyde, phenyl acetaldehyde, benzyl formate, benzyl acetate, cis-3-hexenyl benzoate, methyl hexanoate, hexanal, eucalyptol, eugenol, acetaldehyde, ethyl acetate, ethyl butyrate, turpentine gum oil, limonene, gum caphor, isobornyl acetate, borneol, cinnamic aldehyde, cumminic aldehyde, cuminic aldehyde, furfural, methyl cinnamate, cassia oil, vanillin, maltol, parahydroxybenzyl acetone, dimethyl sulfide, alpha-ionone, acetic acid, isobutyl acetate, acetone, butyric acid, formic acid, valeric acid, amyl acetate, amyl butyrate, anethol, benzyl salicylate, diacetyl, dimethyl anthranilate, ethyl methylphenylglycidate, ethyl succinate, ethyl valerate, geraniol, cis-3-hexen-1-ol, 2-hexenyl acetate, 2-hexenyl butyrate, hexyl butyrate, 4-(p-hydroxyphenyl)-2-butanone, beta-ionone, isobutyl cinnamate, jasmine, lemon essential oil, methyl butyrate, methyl caproate, methyl disulfide, methyl p-naphthyl ketone, orris butter, rose absolute, terpenyl acetate, gamma-undecalactone, vanilla and alcohol.

The specific flavoring adjuvant selected for use may be either solid or liquid depending upon the desired physical form of the ultimate product, i.e., foodstuff, whether simulated or natural, and should, in any event, (i) be organoleptically compatible with the 6-hydroxy-2,6-dimethylheptanal of our invention by not covering or spoiling the organoleptic properties (aroma and/or taste) thereof; (ii) be nonreactive with the 6-hydroxy-2,6-dimethylheptanal of our invention and (iii) be capable of providing an environment in which the 6-hydroxy-2,6-dimethylheptanal can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 6-hydroxy-2,6-dimethylheptanal employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition whether foodstuff per se, chewing gum, per se, medicinal product per se, toothpaste per se, or flavoring composition.

The use of insufficient quantities of 6-hydroxy-2,6-dimethylheptanal will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found tht quantities of 6-hydroxy-2,6-dimethylheptanal ranging from a small but effective amount, e.g., 0.5 parts per million up to about 500 parts per million based on total composition are suitable. Concentrations in excess of the maximum quantity stated are not normally recommended, since they fail to provide commensurate enhancement of organoleptic properties. In those instances, wherein the 6-hydroxy-2,6-dimethylheptanal or stereoisomer thereof of our invention added to the foodstuff as an integral component of a flavoring composition, it is, of course, essential that the total quantity of flavoring composition employed be sufficient to yield an effective 6-hydroxy-2,6-dimethylheptanal concentration in the foodstuff product.

Food flavoring compositions prepared in accordance with the present invention preferably contain the 6-hydroxy-2,6-dimethylheptanal in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 6-hydroxy-2,6-dimethylheptanal with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and 6-hydroxy-2,6-dimethylheptanal in a dry blender until the requisite degree of uniformity is achieved.

It is presently preferred to combine with the 6-hydroxy-2,6-dimethylheptanal (or stereoisomer thereof) of our invention, the following adjuvants:

Heliotropin;
Terpinenol-4;
Benzaldehyde;
Anisaldehyde;
Phenyl acetaldehyde;
Benzyl formate;
Benzyl acetate;
Cis-3-hexenyl benzoate;
Methyl hexanoate;
Hexanal;
Eucalyptol;
Eugenol;
Acetaldehyde;

Ethyl acetate;
Ethyl butyrate;
Turpentine gum oil;
Limonene;
Gum camphor;
Iosbornyl acetate;
Borneol;
Cinnamic aldehyde;
Cuminic aldehyde;
Furfural;
Methyl cinnamate;
Cassia oil;
Vanillin;
Maltol;
Parahydroxybenzylacetone;
Dimethyl sulfide;
Alpha-ionone;
Acetic acid;
Isobutyl acetate;
Acetone;
Butyric acid;
Formic acid;
Valeric acid;
Amyl acetate;
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;
2-Hexenyl butyrate;
Hexyl butyrate;
4-(p-Hydroxyphenyl)-2-butanone;
Beta-ionone;
Isobutyl cinnamate;
β-Damascenone
β-Damascone
Black raspberry juice extract;
Natural raspberry extract;
Methyl butyrate;
Methyl caproate;
Orris butter;
Rose absolute;
Terpenyl acetate;
Gamma-undecalactone,
Vanilla; and
Alcohol.

An additional aspect of our invention provides an organoleptically improved smoking tobacco product and additives therefor, as well as methods of making the same which overcome problems heretofore encountered in which specific desired sweet, woody, piney and fruity flavor characteristics of natural tobacco (prior to smoking and, on smoking, in the mainstream and in the sidestream) as well as cooling effects, are created or enhanced or modified or augmented and may be readily controlled and maintained at the desired uniform level regardless of variations in the tobacco components of the blend.

This invention further provides improved tobacco additives and methods whereby various desirable natural aromatic tobacco flavoring characteristics with sweet, fruity, melon-like, peach-like and floral notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient the 6-hydroxy-2,6-dimethylheptanal (or stereoisomer thereof) of our invention.

In addition to the 6-hydroxy-2,6-dimethylheptanal of our invention other flavoring and aroma additives may be added to the smoking tobacco material or substitute therefor either separately or in admixture with the 6-hydroxy-2,6-dimethylheptanal as follows:

I. Synthetic Materials:
  Beta-ethyl-cinnamaldehyde;
  Eugenol;
  Dipentene;
  Damascenone;
  Maltol;
  Ethyl maltol;
  Delta undecalactone;
  Delta decalactone;
  Benzaldehyde;
  Amyl acetate;
  Ethyl butyrate;
  Ethyl valerate;
  Ethyl acetate;
  2-Hexenol-1;
  2-Methyl-5-isopropyl-1,3-nonadiene-8-one;
  2,6-Dimethyl-2,6-undecadiene-10-one;
  2-Methyl-5-isopropylacetophenone;
  2-Hydroxy-2,5,5,8a-tetramethyl-1-(2-hydroxyethyl)-decahydronaphthalene;
  Dodecahydro-3a,6,6,9a-tetramethyl-naphtho-(2,1b)-furan
  4-Hydroxyhexanoic acid, gamma lactone; and
  Polyisoprenoid hydrocarbons defined in Example V of U.S. Pat. No. 3,589,372 issued on June 29, 1971.

II. Natural Oils:
  Celery seed oil;
  Coffee extract;
  Bergamot Oil;
  Cocoa extract;
  Nutmeg Oil; and
  Origanum Oil.

An aroma and flavoring concentrate containing the 6-hydroxy-2,6-dimethylheptanal (or stereoisomer thereof) of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of sweet, fruity melon-like, peach-like, floral and aromatic sweet tobacco-like notes, we have found that satisfactory results are obtained if the proportion by weight of the sum total of 6-hydroxy-2,6-dimethylheptanal (or stereoisomer thereof) to smoking tobacco material is between 50 ppm and 1,500 ppm (0.005%–0.15%). We have further found that satisfactory results are obtained if the proportion by weight of the sum total of 6-hydroxy-2,6-dimethylheptanal used to flavoring material is between 1,500 and 15,000 ppm (0.15%–1.5%).

Any convenient method for incorporating the 6-hydroxy-2,6-dimethylheptanal into the tobacco product may be employed. Thus, the 6-hydroxy-2,6-dimethylheptanal taken alone or along with other flavoring additives may be dissolved in a suitable solvent such as ethanol, diethyl ether and/or volatile organic solvents and the resulting solution may either be spread on the cured, cased and blended tobacco material or the tobacco material may be dipped into such solution. Under certain circumstances, a solution of the 6-hydroxy-2,6-dimethylheptanal taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the 6-hydroxy-2,6-dimethylheptanal in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of 6-hydroxy-2,6-dimethylheptanal (racemic mixture) having the structure:

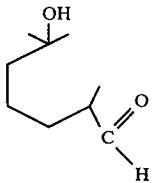

in an amount to provide a tobacco composition containing 800 ppm by weight of 6-hydroxy-2,6-dimethylheptanal on a dry basis. Thereafter, the alcohol is removed by evaporation and the tobacco is manufactured into cigarettes by the usual techniques. The cigarette when treated as indicated has a desired and pleasing aroma which is detectable in the main and sidestreams when the cigarette is smoked. This aroma is described as being sweeter, more aromatic, more tobacco-like and having sweet, fruity notes.

While our invention is particularly useful in the manufacture of smoking tobacco, such as cigarette tobacco, cigar tobacco and pipe tobacco, other tobacco products, formed from sheeted tobacco dust or fines may also be used. Likewise, the 6-hydroxy-2,6-dimethylheptanal of our invention can be incorporated with materials such as filter tip materials (e.g. cellulose acetate filters wherein fruity-melon-like, peach-like, sweet, floral, sweet aromatic tobacco-like effects are desired), seam paste, packaging materials and the like which are used along with tobacco to form a product adapted for smoking. Furthermore, the 6-hydroxy-2,6-dimethylheptanal can be added to certain tobacco substitutes of natural or synthetic origin (e.g., dried lettuce leaves) and, accordingly, by the term "smoking tobacco" as used throughout this specification is meant any composition intended for human consumption by smoking whether composed of tobacco plant parts or substitute materials or both.

The 6-hydroxy-2,6-dimethylheptanal and one or more auxiliary perfume ingredients, including, for example, hydrocarbons, alcohols, (other than the 6-hydroxy-2,6-dimethylheptanal of our invention) ketones, aldehydes, (other than the 6-hydroxy-2,6-dimethylheptanal of our invention) nitriles, esters, lactones or cyclic esters, synthetic essential oils and natural essential oils, may be admixed so that the combined odors of the individual components produce a pleasant and desired fragrance, particularly and preferably in berry fruit-type or floral fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more of the 6-hydroxy-2,6-dimethylheptanal of our invention can be used to alter, modify or enhance the aroma characteristics of a perfume composition, for example, by utilizing or moderating the olfactory reaction contributed by another ingredient in the composition.

The amount of 6-hydroxy-2,6-dimethylheptanal of our invention which will be effective in perfume compositions as well as in perfumed articles and colognes depends on many factors, including the other ingredients, their amounts and the effects which are desired. It has been found that perfume compositions containing a little as 0.01% of 6-hydroxy-2,6-dimethylheptanal or even less (e.g., 0.005%) can be used to impart a sweet, green, melony, floral, muguet-like to soaps, cosmetics, detergents (including anionic, nonionic and cationic detergents) or other products. The amount employed can range up to 70% of the fragrance components and will depend on considerations of cost, nature of the end product, the effect desired on the finished product and the particular fragrance sought.

The 6-hydroxy-2,6-dimethylheptanol of our invention is useful (taken alone or together with other ingredients in perfume compositions) in nonionic, anionic and cationic detergents and soaps, fabric softener compositions (particularly those fabricated into articles for use in automatic clothes dryers), space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. As little as 0.1% of 6-hydroxy-2,6-dimethylheptanal will suffice to impart an intense sweet green melony floral note to muguet or berry fruit perfume formulations and perfumed articles, e.g. soaps, detergents and fabric softener compositions. Generally, no more than 3% of 6-hydroxy-2,6-dimethylheptanal based on the ultimate end product, is required in the perfume composition or perfumed article, e.g. the soap or detergent.

In addition, the perfume composition or fragrance composition of our invention can contain a vehicle, or carrier for the 6-hydroxy-2,6-dimethylheptanal. The vehicle can be a liquid such as a non-toxic alcohol, (e.g. ethanol) a non-toxic glycol, (e.g. propylene glycol) or the like. The carrier can also be an absorbent solid, such as a gum (e.g., gum arabic), or components for encapsulating the composition (such as gelatin) as, for example, by means of coacervation.

It will thus be apparent that the 6-hydroxy-2,6-dimethylheptanal of our invention can be utilized to alter, modify or enhance sensory properties, particularly or- ganoleptic properties, such as flavor(s) and/or fragrance(s) of a wide variety of consumable materials.

The following examples serve to illustrate specific embodiments of our invention.

It will be understood that these Examples are illustrative and the invention is to be considered restricted thereto only as indicated in the appended claims.

EXAMPLE I

Preparation of 2,6-Dimethyl-5-Heptanal Reaction

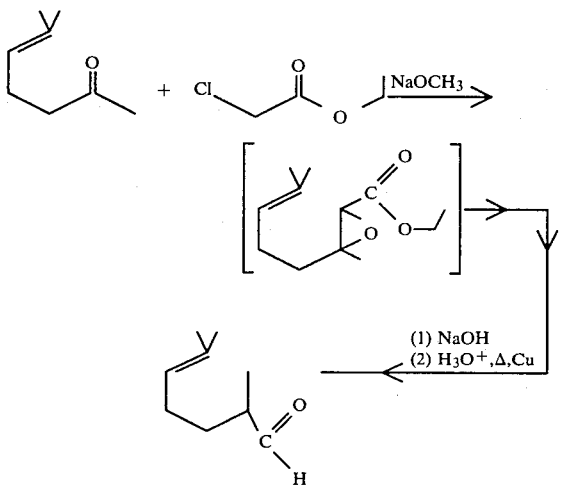

Sodium methoxide (604 grams) is added positionwise over a 1-hour period to a stirred slurry of 1008 grams of 6-methyl-5-hepten-2-one and 1225 grams of ethyl chloroacetate at −10° C. The resulting thick slurry is stirred for an additional 1.5 hours at −10° C. A solution of 720 grams of sodium hydroxide in 4400 mls of methanol is then slowly added and the resulting solution is heated at 50° C. for 2 hours. The reaction mass is then poured into 12 liters of water with stirring. The aqueous reaction mass is extracted twice with 300 mls toluene. The toluene extracts are discarded and the aqueous layer is acidified with 1200 mls of concentrated HCl (accompanied by evolution of carbon dioxide). The aqueous layer is extracted with three 1 liter portions of toluene. The combined toluene extracts are washed with 2 liter of water. The toluene is removed by distillation at reduced pressure. 10 grams of copper powder are added to the concentrated organic extract. Distillation under vacuum accompanied by release of carbon dioxide affords fractions containing 657 grams of 2,6-dimethyl-5-heptenal.

The product is further purified by fractional distillation through a 1.5"×12" Goodloe packed column to afford a product consisting of 92% 2.6-dimethyl-5-heptenal and 8% 2,6-dimethyl-5-hexen-2-one (b.p. 88°, 30 mm).

FIG. 1 is the GC profile of the reaction mass after addition of sodium methoxide (180° isothermal, 10% SE-30 packed column).

Figure 2:
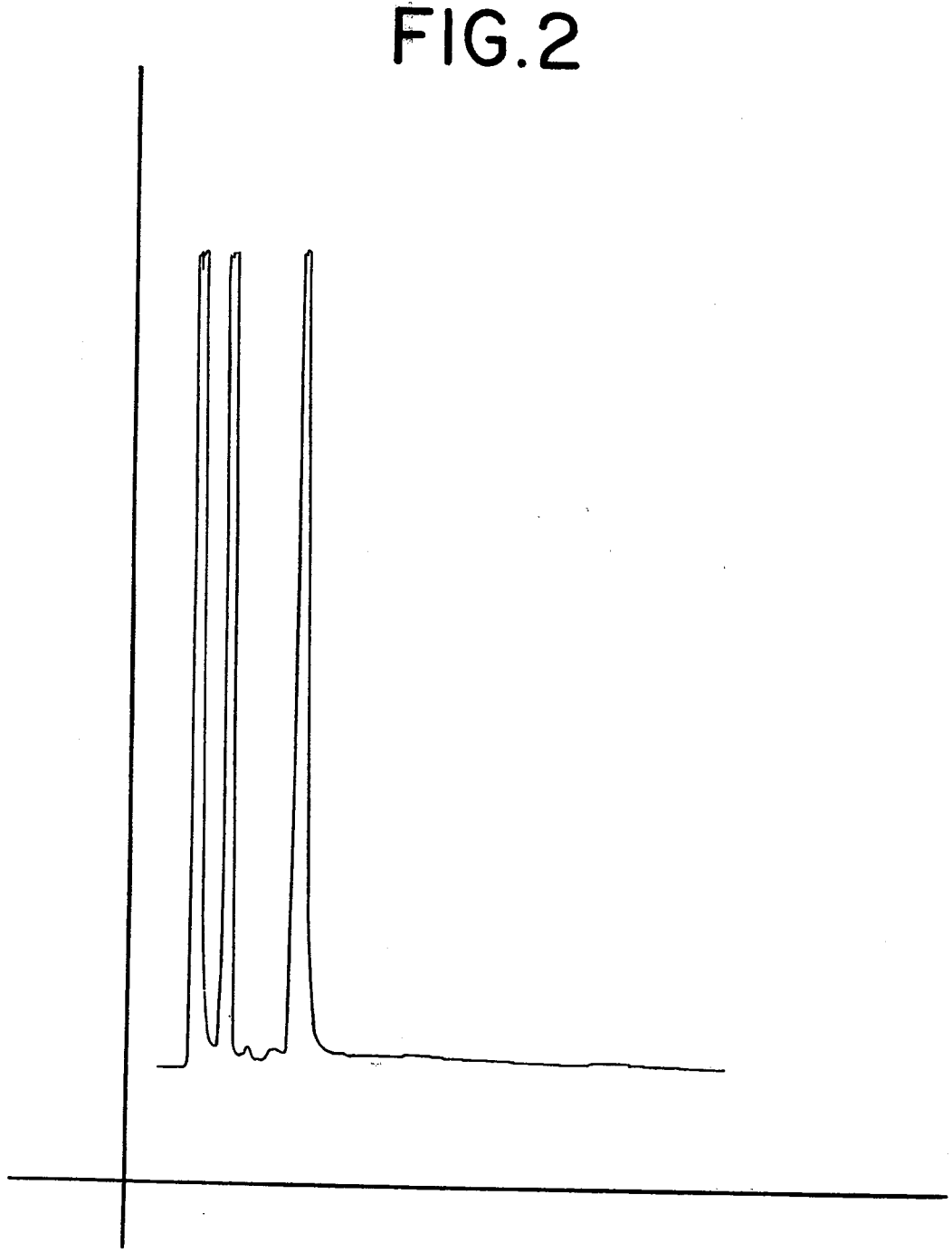
FIG. 2 is the GC profile of the reaction mass of Example I after acidification with hydrochloric acid whereby a reaction product containing 2,6-dimethyl-5-heptenal is formed.

FIG. 2 is the GC profile of the reaction mass after acidification with HCl (the intermediate glycidic acid formed at this stage decarboxylates on the GC to form the product, 2,6-dimethyl-5-heptenal). Conditions: 180° isothermal; 10% SE-30 packed column.

EXAMPLE II

Preparation of 2,6-Dimethyl-6-Hydroxy Heptanal Reaction

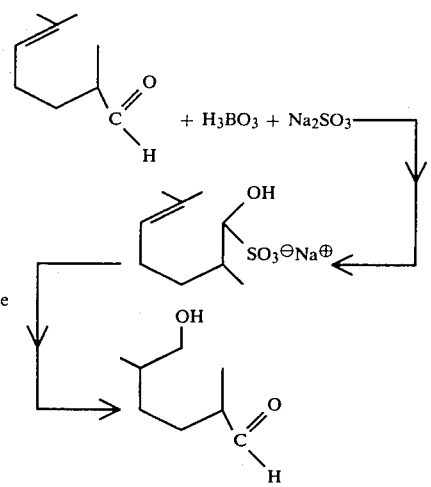

Figure 3:
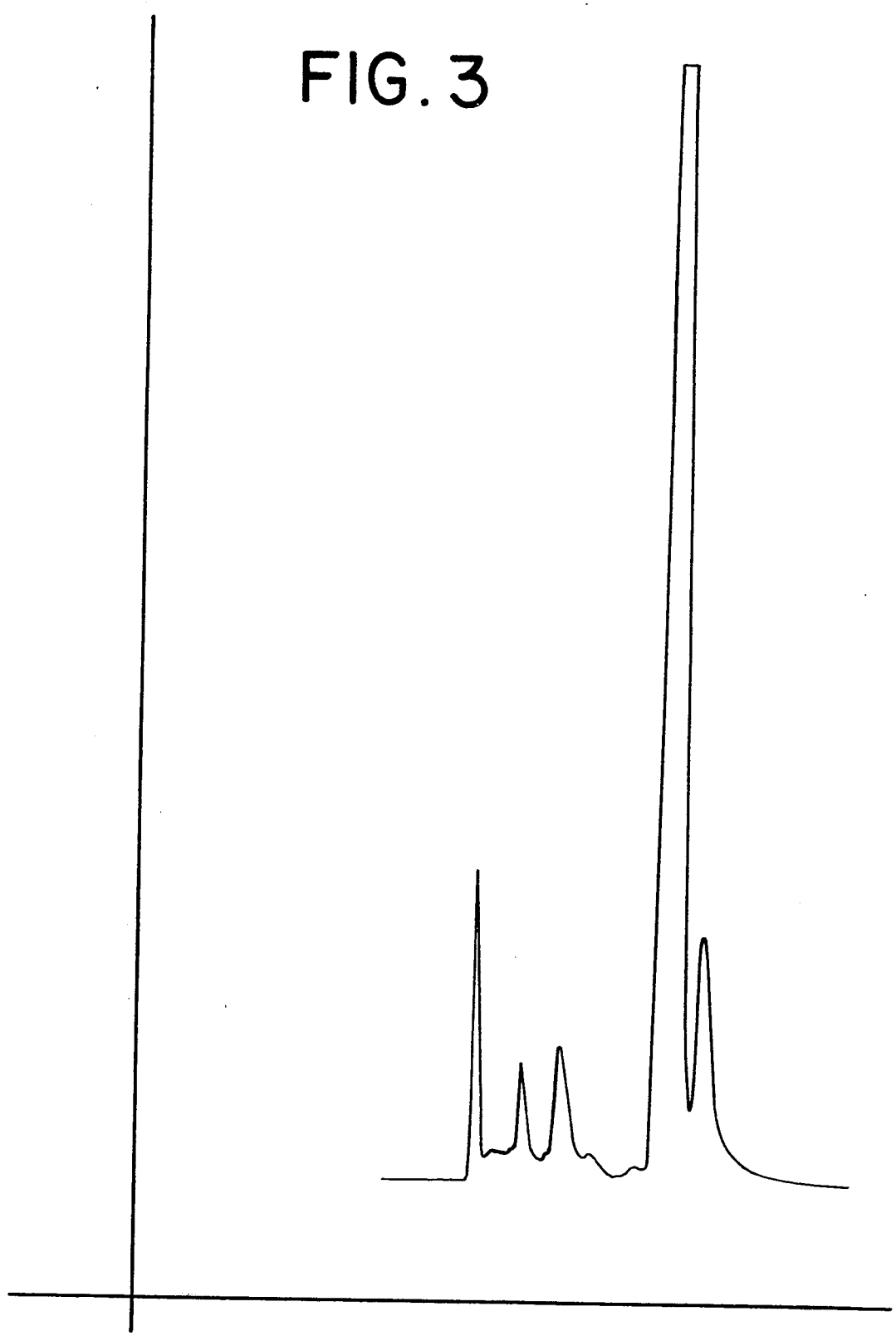
FIG. 3 is the GC profile for the reaction product of Example II prior to fractional distillation wherein 2,6-dimethyl-6-hydroxy heptanal is formed and contained in the reaction product.

An aqueous emulsion of 2,6-dimethyl-5-heptenal is prepared by stirring a solution of 3 grams of sodium oleate, and 400 mls of water, with 490 grams 2,6-dimethyl-5-heptenal. The emulsion is added at 250° C. to a solution comprising 1072 grams of sodium sulfite, 326 grams of boric acid and 5 liters of water. The resulting mixture is stirred for two hours resulting in the formation of a white flocculant solid. To this reaction mass is added 3000 mls of 30% hydrochloric acid. The addition is accompanied by release of sulfur dioxide fumes and a temperature rise to 30° C. Stirring is continued for 30 minutes whereupon a clear liquid is formed. Over a 30 minute period, 1783 grams of sodium carbonate is added accompanied by release of carbon dioxide. The reaction mixture is extracted twice with 500 ml portions of toluene. The toluene extracts are washed with water and distilled to afford 2,6-dimethyl-6-hydroxy heptanal (249 grams). The GC profile for this material is set forth in FIG. 3. Fractional distillation through a 1.5"×12" Goodloe column affords the pure product (b.p. 112° C., 4 mm).

Figure 4:
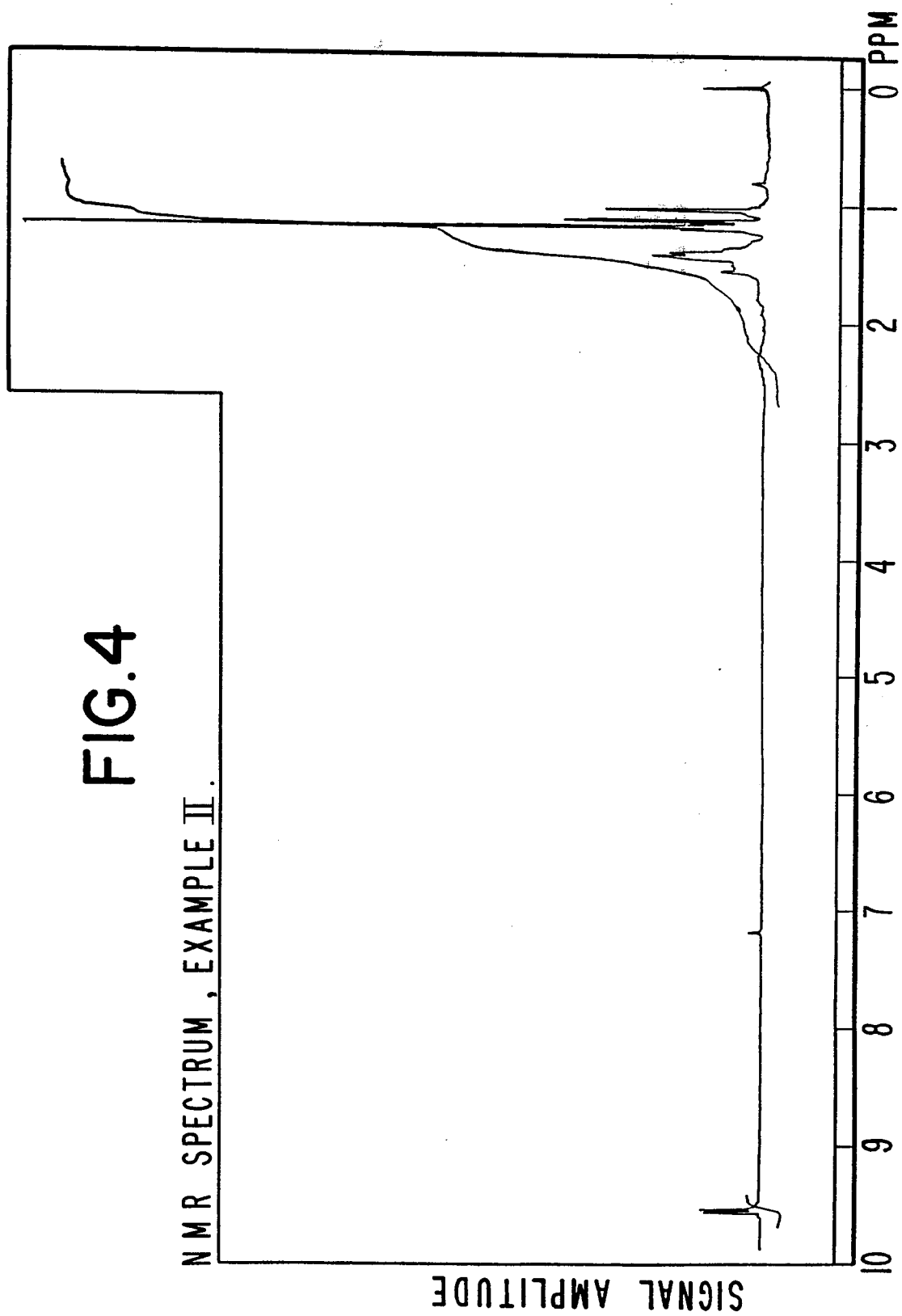
FIG. 4 is the NMR spectrum for 2,6-dimethyl-6-hydroxy heptanal produced according to Example II.

The NMR spectrum of 2,6-dimethyl-6-hydroxyheptanal is shown in FIG. 4.

Figure 5:
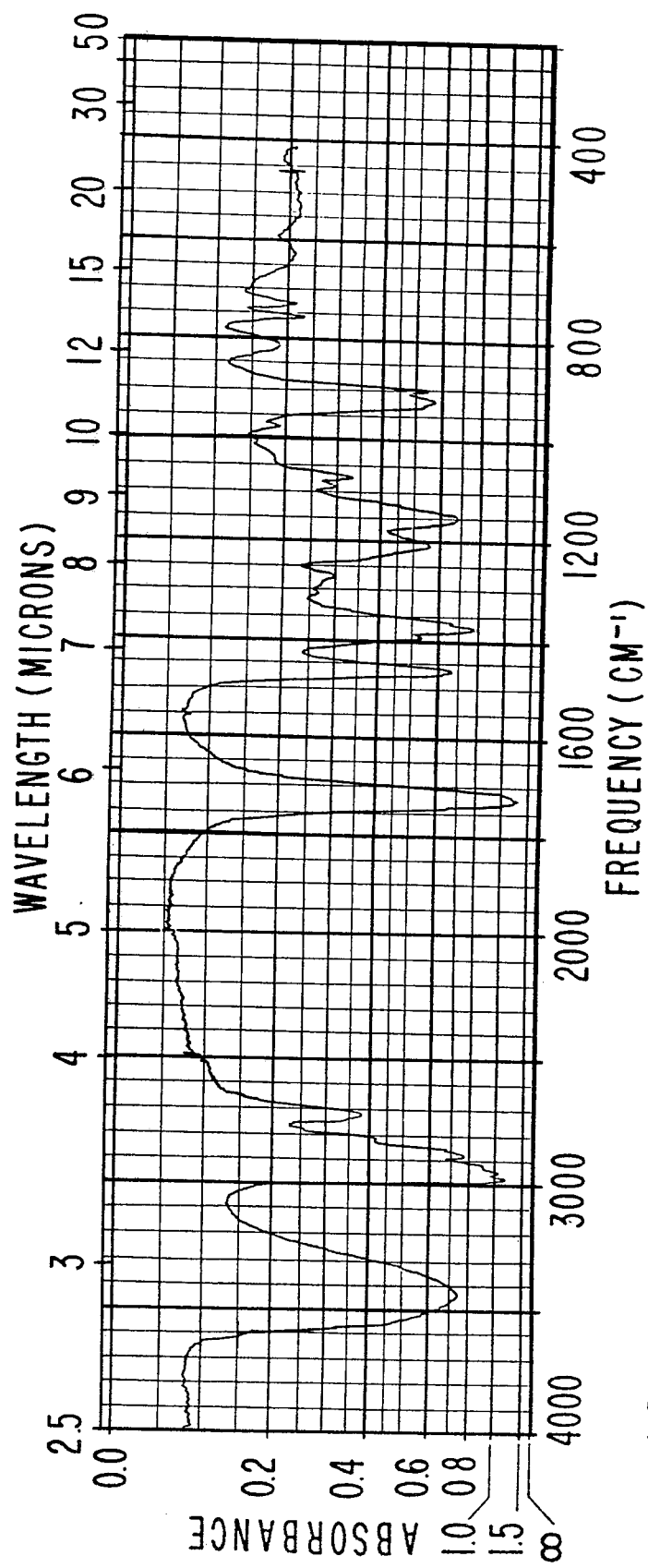
FIG. 5 is the infrared spectrum for 2,6-dimethyl-6-hydroxy heptanal produced according to Example II.
Figure 6:
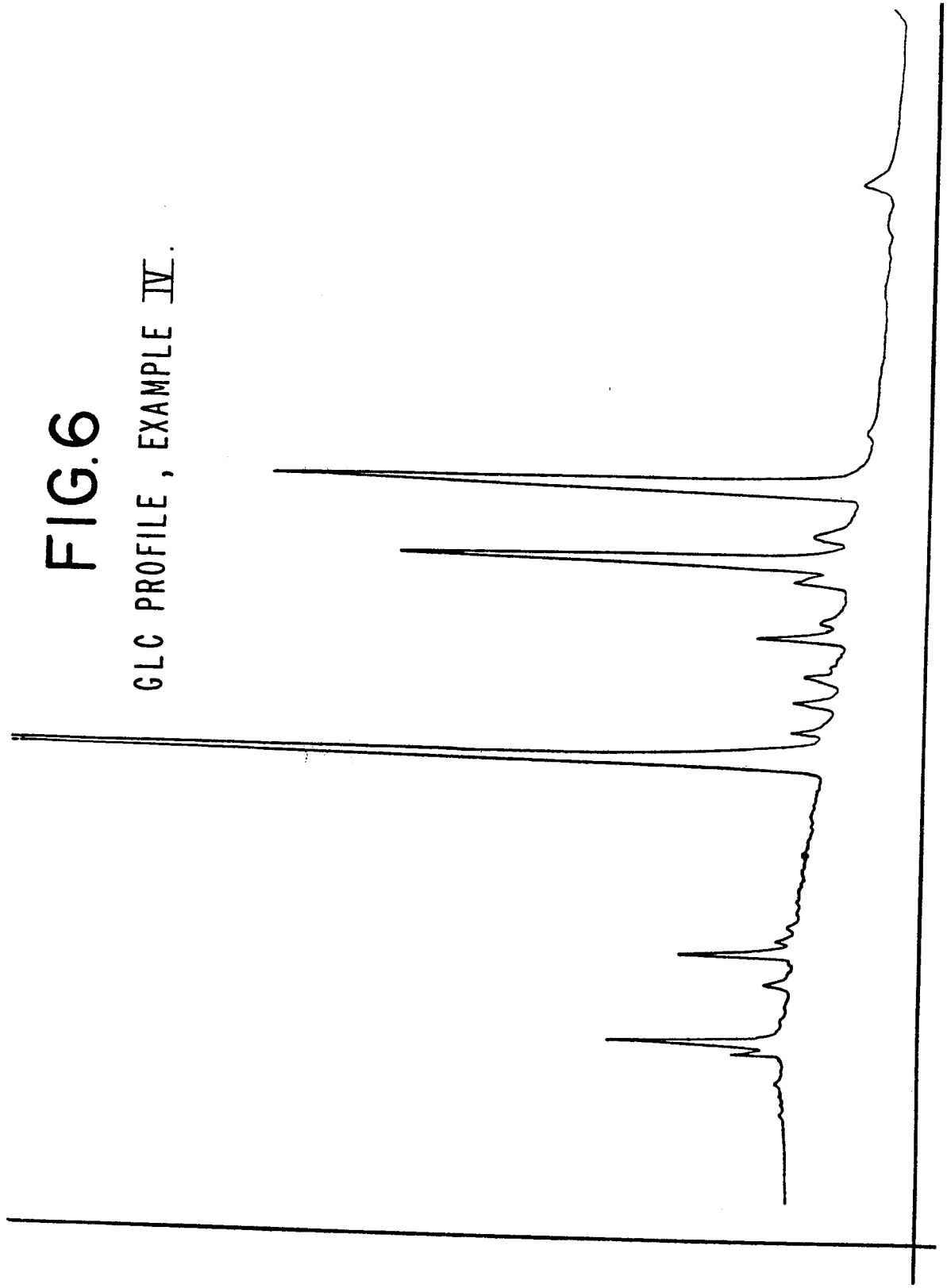
FIG. 6 is that portion of the GLC profile of *Java Citronella Oil* which contains 2,6-dimethyl-5-heptenal.

The IR spectrum of 2,6-dimethyl-6-hydroxyheptanal is shown in FIG. 5.

The resulting racemate is separated into its optical isomers; the "d" and "l" isomers, by means of treatment thereof with an equimolar quantity of optically pure d-alanine. The resulting Shiff bases are separated by means of fractional crystallization from aqueous ethanol and the pure d-d and d-l Shiff bases are hydrolyzed separately using 8% aqueous sodium hydroxide thereby yielding the pure stereoisomers which are recrystallized from their respective hydrolyzate solutions.

EXAMPLE III

Preparation of 2,6-Dimethyl-6-Hydroxyheptanal Reaction

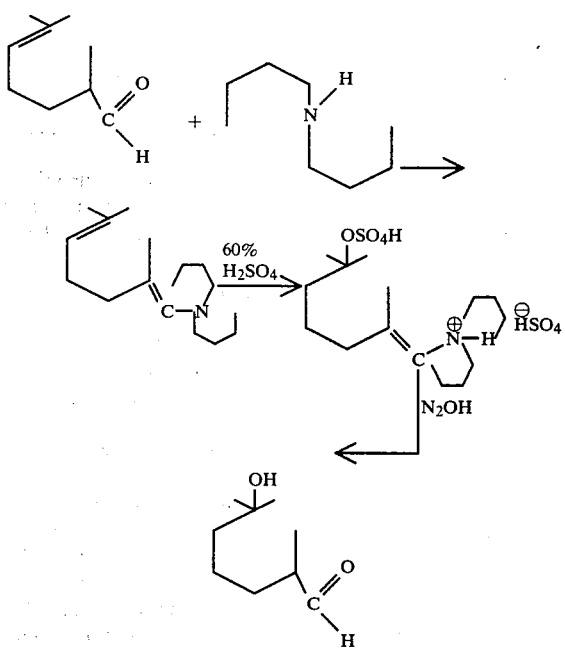

A solution of 800 mls of toluene, 420 grams of 2,6-dimethyl-5-heptenal, and 366 grams of dibutyl amine are heated at reflux for 2.5 hours. A Dean Stark trap is used to remove 34 mls of water. The solution is then cooled and distilled under vacuum to afford 715 grams of 2.6-dimethyl-1,5-heptadienyl dibutylenamine. The 2,6-dimethyl-1,5-heptadienyldibutylenamine is then dropwise added to a 1200 grams of 66% sulfuric acid at 10°–15° C. over a 1 hour period. The reaction mass is stirred for an additional 15 minutes and poured into a stirred, cooled mixture containing 6 liters of water, 720 grams of sodium hydroxide and 500 mls of toluene. The temperature rises from an initial 10° C. to 35° C. The reaction mass is stirred for one hour. The organic layer is separated and the aqueous layer is extracted with 300 mls of toluene. The combined organic extracts are washed twice with water and distilled to afford 356 grams of 2,6-dimethyl-6-hydroxyheptanal (b.p. 105° C., 3.5 mm).

EXAMPLE IV

Identification of 2,6-Dimethyl-6-Hydroxyheptanal in Citronella Java Oil

One hundred grams of Citronella Java Oil is vacuum distilled on an 8" micro distillation column to yield 49 fractions. Fractions 20–27 (4 g) are combined and column chromatographed (100 g 95% $SiO_2$, 5% water) using isopentane as an eluant. A peak corresponding to 2,6-dimethyl-6-hydroxyheptanal in the isopentane eluant is then trapped 25 times on a 10'×⅛"10% carbowax 20 M column and then rechromatographed on a 500'×0.3" SE-30 capillary column. A peak with the same retention time on the capillary column is isolated and analyzed by IR and MS spectra which are found to be superimposable with those of a reference sample of 2,6-dimethyl-6-hydroxyheptanal.

EXAMPLE V

Isolation and Identification of 2,6-Dimethyl-6-Hydroxy-5-Heptanal from Laurine ® (Trademark of Givaudan Corporation of Clifton New Jersey)

Figure 7:
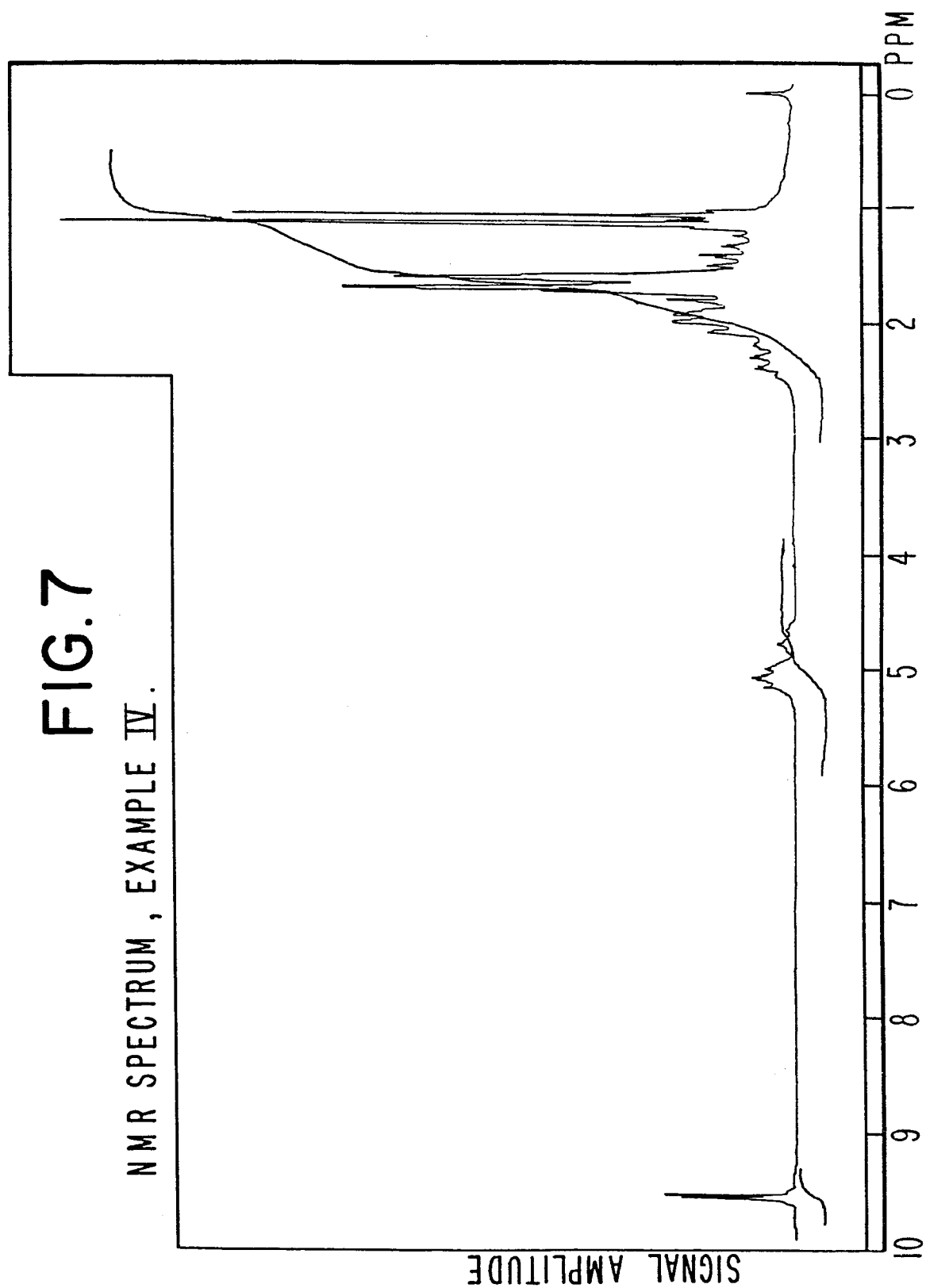
FIG. 7 is the NMR spectrum for 2,6-dimethyl-5-heptenal produced from Java Citronella Oil according to Example IV.
Figure 8:
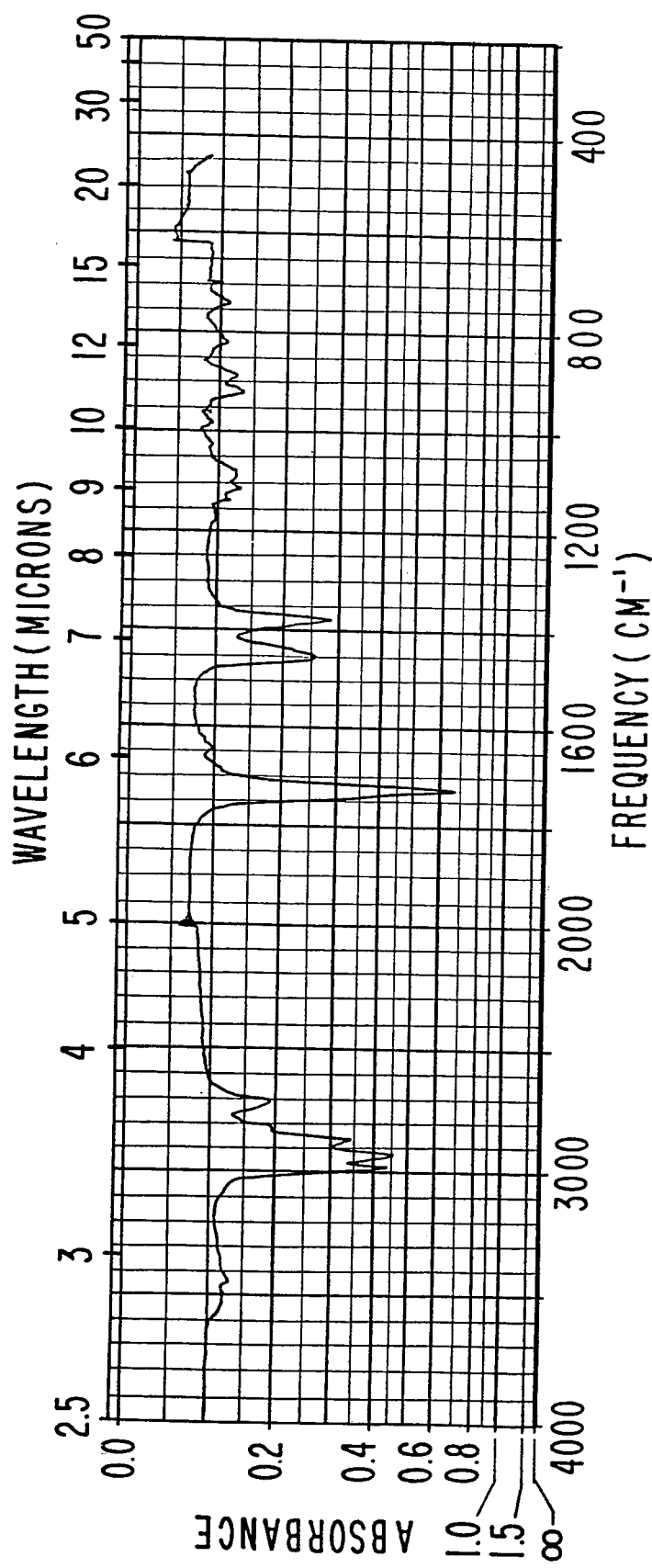
FIG. 8 is the infrared spectrum for 2,6-dimethyl-5-heptenal produced from Java Citronella Oil according to Example IV.

1500 grams of Laurine ® (trademark of Givaudan Corporation) available from Givaudan Corporation of Clifton, New Jersey, are charged to a distillation flask. The material is fractionated through a 36"×1" Goodloe packed column at a reflux ratio of 19:1. Three 5 gram fractions are collected. The second fraction (b.p. 95°, 1.0 mm) is analyzed by GC (see FIG. 9). A GC peak comprising 7.8% of the total mixture has the identical elution time as 2,6-dimethyl-6-hydroxyheptanal. The indicated peak in FIG. 7 is trapped in a glass capillary tube. NMR and IR spectra are consistent with the assignment of the compound 2,6-dimethyl-6-hydroxyheptanal to the indicated peak. The spectra are identical to those shown in FIGS. 4 and 5.

FIG. 9 represents the GLC spectrum for fraction 2 (10% carbowax 20 M ⅛"×10" packed column; 80°–200° C., 2° C./min program).

EXAMPLE VI

Flavor Formulation Containing 6-Hydroxy-2,6-Dimethylheptanal

The following raspberry formulation is prepared:

| Ingredient | Parts by Weight |
| --- | --- |
| Parahydroxy benzyl acetone | 5 |
| Vanillin | 15 |
| Maltol | 20 |
| Ethyl-3-methyl-3-phenyl glycidate | 15 |
| Ethyl acetate | 13 |
| Ethyl butyrate | 20 |
| Methyl cinnamate | 5 |
| Methyl anthranilate | 1 |
| Ethyl benzoate | 1 |
| Gamma undecalactone | 2 |
| Diacetyl | 2 |
| Anethol | 1 |
| Cis-3-hexenol | 20 |
| 95% aqueous ethanol | 180 |
| Propylene glycol | 700 |
| | 1000 |

To a portion of the foregoing formulation, 4% by weight of 6-hydroxy-2,6-dimethylheptanal prepared according to the process of Example II is added. The formulation with the 6-hydroxy-2,6-dimethylheptanal is compared to the same formulation without said 6-hydroxy-2,6-dimethylheptanal.

Both flavors are evaluated in water at the rate of 50 ppm. Both beverages are tasted by an expert panel. The beverage containing the raspberry formulation with the addition of 6-hydroxy-2,6-dimethylheptanal is unanimously preferred as having fresh raspberry and a sweet-raspberry aroma and taste missing in the basic raspberry formulation.

EXAMPLE VII

Tobacco Flavor Formulation and Tobacco

A tobacco mixture is produced by admixing the following materials:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes having cellulose acetate filters are prepared from this tobacco.

The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. One-third of the cigarettes are then treated in the tobacco section thereof with 5 ppm of 6-hydroxy-2,6-dimethylheptanal produced according to the process of Example II. One-third of the cigarettes are treated on the cellulose acetate filter with 1 microliter of a 0.1% ethanol solution of 6-hydroxy-2,6-dimethylheptanal produced according to Example II.

The control cigarettes not containing any 6-hydroxy-2,6-dimethylheptanal produced according to the process of Example II and the experimental cigarettes which do contain 6-hydroxy-2,6-dimethylheptanal produced according to the process of Example II are evaluated by three-way comparison, and the results are as follows:

In aroma, the cigarettes containing the 6-hydroxy-2,6-dimethylheptanal in the tobacco or in the filter have been found to be sweeter and fruitier.

In smoke flavor, the cigarettes containing the 6-hydroxy-2,6-dimethylheptanal are more aromatic, more sweet, fruitier and slightly less harsh in the mouth and throat. In addition, those cigarettes containing the 6-hydroxy-2,6-dimethylheptanal in the tobacco give rise to a woody nuance in the taste and aroma in smoking.

EXAMPLE VIII

Raspberry Fragrance

The following mixture is prepared:

| Ingredient | Parts by Weight |
|---|---|
| Cuminic acetate | 15 |
| Ethyl acetoacetate | 3 |
| Ethyl laurate | 30 |
| Cinnamyl isobutyrate | 15 |
| Cinnamyl decylate | 20 |
| Diacetyl (10% in 95% aqueous ethanol) | 2 |
| Ethyl pelargonate | 5 |
| Gamma undecalactone | 20 |
| Ethyl isobutyrate | 110 |
| Ethyl isovalerate | 60 |
| Ethyl heptanoate | 12 |
| Dulicinyl | 5 |
| 2(para-hydroxyphenyl)-3-butanone | 2 |

-continued

| Ingredient | Parts by Weight |
|---|---|
| Ethyl acetate | 5 |
| Beta-ionone | 5 |
| Palatone | 3 |
| Vanillin | 10 |
| Ethyl vanillin | 10 |
| Ethyl-3-methyl-3-phenyl glycidate | 70 |
| 6-hydroxy-2,6-dimethylheptanal prepared according to the process of Example II | 10 |

The mixture containing 6-hydroxy-2,6-dimethylheptanal prepared according to the process of Example II imparts the green floral aroma necessary to the fresh raspberry aroma.

EXAMPLE IX

Preparation of Soap Composition

One hundred grams of soap chips produced according to Example V of U.S. Pat. No. 4,058,487, issued on Nov. 15, 1977 as follows:

The sodium salt of an equal mixture of $C_{10}$–$C_{14}$ alkane sulfonates (95% active), 40 pounds is dissolved in a mixture of 80 pounds of anhydrous isopropanol and 125 pounds of deionized water at a 150° F. In this mixture is dissolved 10 pounds of partially hydrogenated coconut oil fatty acids and 15 pounds of sodium mono-$C_{14}$-alkyl maleate and the pH of this solution is adjusted to 6.0 by the addition of a small amount of 50% aqueous solution of sodium hydroxide. The isopropanol is disstilled off and the remaining aqueous solution is drum dried. The resulting solid actives are then blended in a chip mixer with 10 pounds of water and 0.2 pounds of titanium hydroxide are mixed with one gram of the perfume composition of Example VIII until a substantially homogeneous composition is obtained. The perfumed soap composition manifests an excellent raspberry character with a green floral muguet undertone.

EXAMPLE X

Preparation of a Detergent Composition

A total of 100 g of a detergent powder prepared according to U.S. Pat. No. 4,058,472 and containing:

5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol and 40 parts by weight of di-$C_{14}$–$C_{18}$ alkyl catechol, 35% of sodium tetrapyrophosphate, 30% of sodium silicate, 20% of sodium carbonate, 3% of sodium carboxymethylcellulose and 7% of starch is mixed with 0.15 g of the perfume composition of Example VIII until a substantially homogeneous composition is obtained. This composition has an excellent raspberry character with a green floral muguet undertone.

EXAMPLE XI

Preparation of a Cosmetic Powder Composition

A cosmetic powder is prepared by mixing in a ball mill, 100 g of talcum powder with 0.25 g of the 6-hydroxy-2,6-dimethylheptanal prepared according to Example II. It has an excellent, sweet, green, floral muguet aroma.

EXAMPLE XII

Perfumed Liquid Detergent

Concentrated liquid detergents with a fruity, raspberry odor are prepared containing 0.10%, 0.15% and 0.20% of 6-hydroxy-2,6-dimethylheptanal prepared according to Example II. They are prepared by adding and homogeneously mixing the appropriate quantity of 6-hydroxy-2,6-dimethylheptanal in the liquid detergent. The detergents all possess an excellent sweet, green, floral muguet fragrance the intensity increasing with greater concentrations of 6-hydroxy-2,6-dimethylheptanal.

EXAMPLE XIII

Preparation of a Cologne and Handerchief Perfume

The composition of Example VIII is incorporated in a cologne at a concentration of 2.5% in 85% aqueous ethanol; and into a handkerchief perfume at a concentration of 20% (in 95% aqueous ethanol). The use of the mixture containing 6-hydroxy-2,6-dimethylheptanal in the composition of example VIII affords a distinct and definite strong raspberry aroma with an excellent green, floral, muguet-like undertone to the handkerchief perfume and cologne.

EXAMPLE XIV

Preparation of Soap Composition

One hundred grams of soap chips produced according to Example V of U.S. Pat. No. 4,058,487 (as set forth in Example IX, supra) are mixed with one gram of 6-hydroxy-2,6-dimethylheptanal produced according to Example II until a substantially homogeneous composition is obtained. The perfumed soap composition manifests an excellent sweet, green, floral muguet aroma.

EXAMPLE XV

Preparation of a Detergent Composition

A total of 100 g of a detergent powder produced according to U.S. Pat. No. 4,058,472 (as set forth in Example X, supra) is mixed with 0.15 g of the mixture containing 6-hydroxy-2,6-dimethylheptanal of Example II until a substantially homogeneous composition is obtained. This composition has an excellent sweet, green floral muguet aroma.

EXAMPLE XVI

The following concentrate is prepared:

| Ingredient | Parts by Weight |
| --- | --- |
| Geraniol | 1.00 |
| Ethyl methyl phenyl glycidate | 3.33 |
| 6-hydroxy-2,6-dimethylheptanal prepared according to the process of Example II) | 4.77 |
| Vanillin | 5.66 |
| Ethyl pelargonate | 13.06 |
| Isoamyl acetate | 14.00 |
| Ethyl butyrate | 58.18 |

EXAMPLE XVII

Another concentrate is prepared as follows:

| Ingredient | Parts by Weight |
| --- | --- |
| Naphthyl ethyl ether | 0.96 |
| Vanillin | 2.66 |
| Ethyl methyl phenyl glycidate | 2.88 |
| 6-hydroxy-2,6-dimethylheptanal (prepared according to the process of Example II) | 4.90 |
| Ethyl acetate | 9.58 |
| Isoamyl acetate | 12.25 |
| Ethyl butyrate | 26.20 |
| Isoamyl butyrate | 40.57 |

EXAMPLE XVIII

The concentrate prepared in Example XVI is dissolved in 4 volumes of propylene glycol and the mixture is added to a hard candy melt at the rate of 1.5 oz of the concentrate solution per 100 lbs. of melt. After the finished candy has been produced, it is found to have an excellent raspberry flavor. When the candy is compared with candy made under the same conditions, but without the 6-hydroxy-2,6-dimethylheptanal prepared according to the process of Example II in the concentrate, it is found to have an inferior raspberry flavor.

EXAMPLE XIX

The proplylene glycol solution of the concentrate as prepared in Example XVIII is added to a simple syrup at the rate of ⅛ oz. per gallon of syrup. The syrup is acidified by the addition of 1.5 oz. of 50% aqueous citric acid solution to each gallon of syrup. A carbonated beverage is prepared by admixing one oz. of the flavored, acidified syrup with 5 oz. of carbonated water. The beverage so prepared has an excellent fresh raspberry flavor, and is found to be markedly superior to a beverage prepared in the same manner but without the 6-hydroxy-2,6-dimethylheptanal prepared according to the process of Example II.

EXAMPLE XX

The flavor concentrate prepared in Example XVII is admixed with gum arabic and in the production of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of desserts mix powder. The gelatin dessert produced from the mix has an excellent raspberry flavor and is markedly superior to a gelatin dessert prepared in the same manner without the 6-hydroxy-2,6-dimethylheptanal prepared according to the process of Example II in the concentrate.

EXAMPLE XXI

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:
1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol 20 percent antistatic agent 1 percent of the 6-hydroxy-2,6-dimethylheptanal prepared according to Example II of our invention and giving rise to an excellent sweet, green, floral muguet aroma Fabric-softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aroma as set forth above is imparted in a pleasant manner to the head spaced in the dryer on operation thereof using the said dryer added fabric softening nonwoven fabric.

What is claimed is:

1. A process for preparing 6-hydroxy-2,6-dimethylheptanal defined by one of the structures:

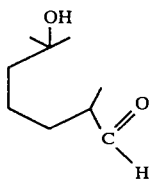

,

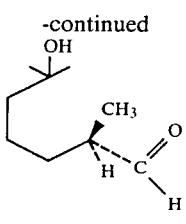

or

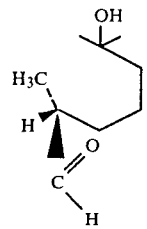

comprising the steps of (1) forming an emulsion of 2,6-dimethyl-5-heptenal with water using an emulsifying agent which is an alkali metal salt of a long chain fatty acid; (2) reacting sodium sulfite with the 2,6-dimethyl-5-heptenal in the presence of boric acid while it is in the emulsion whereby a sulfite-aldehyde addition salt of 2,6-dimethyl-5-heptenal is formed, the reaction taking place at a temperature of between 10° C. and 50° C., the mole ratio of sodium sulfite:2,6-dimethyl-5-heptenal varying between 1:1 up to 10:1; the concentration of sodium sulfite in the reaction mass being from 0.1 molar up to 3.0 molar and the concentration of 2,6-dimethyl-5-heptenal being from 0.5 molar up to 2.0 molar; and (3) hydrolyzing the resulting sulfite-aldehyde addition salt of 2,6-dimethyl-5-heptenal with hydrochloric acid using from 10% up to 50% hydrochloric acid, the mole ratio of HCl:sulfite addition salt of 2,6-dimethyl-6-hydroxyheptanal being 0.5:1 up to 1.5:1 with the reaction temperature for the hydrolysis reaction varying from 0° C. up to 50° C.

* * * * *